United States Patent [19]

Exner

[11] Patent Number: 5,601,995
[45] Date of Patent: Feb. 11, 1997

[54] APPARATUS AND METHOD FOR DETECTING COAGULATION IN BLOOD SAMPLES

[75] Inventor: Thomas Exner, Gordon, Australia

[73] Assignee: Gradipore Limited, North Ryde, Australia

[21] Appl. No.: 397,158
[22] PCT Filed: Sep. 6, 1993
[86] PCT No.: PCT/AU93/00459
§ 371 Date: Mar. 3, 1995
§ 102(e) Date: Mar. 3, 1995
[87] PCT Pub. No.: WO94/06007
PCT Pub. Date: Mar. 17, 1994

[30] Foreign Application Priority Data

Sep. 4, 1992 [AU] Australia .................................. PL4503

[51] Int. Cl.[6] .............................. C12Q 1/56; G01N 31/22
[52] U.S. Cl. .................................. 435/13; 422/56; 422/73; 422/82.02
[58] Field of Search .............................. 73/54.07, 61.54; 204/153.12, 403; 422/56, 69, 73, 82.02, 82.05; 435/13

[56] References Cited

U.S. PATENT DOCUMENTS 3,605,010 9/1971 Folus .................................. 324/30 R
3,695,842 10/1972 Mintz .................................. 23/230 R
5,418,141 5/1995 Zweig et al. .................................. 435/13
5,447,440 9/1995 Davis et al. .................................. 435/6

FOREIGN PATENT DOCUMENTS

72903/87 11/1987 Australia .

*Primary Examiner*—Ralph Gitomer
*Attorney, Agent, or Firm*—Michael J. Striker

[57] ABSTRACT

The method and apparatus are useful for determining a propensity of a blood sample to change from a liquid state to a coagulated state and additionally for measuring the propensity of a coagulated blood sample to lyse. The method includes providing a porous sheet, at least one surface of which contacts an impervious layer; applying the blood sample to an exposed surface of the porous sheet so that the blood sample spreads through a part of the porous sheet; and after the applying of the blood sample to the porous sheet, measuring at least one of a spreading extent and a spreading rate of the blood sample in the porous sheet by measuring either an optical property, an electrical conductivity across the porous sheet, an electrical potential across the porous sheet and an electrical resistance of the porous sheet to determine the propensity of the blood sample to coagulate. The porous sheet can also be impregnated with a clotting agent or a lytic agent to affect the clotting or lysing of the blood sample.

25 Claims, 5 Drawing Sheets

APPARATUS AND METHOD FOR DETECTING COAGULATION IN BLOOD SAMPLES

BACKGROUND OF THE INVENTION

The present invention relates to apparatus and methods for determining the susceptibility of certain liquids to coagulate and subsequently to lyse. The apparatus and methods of the present invention are particularly suitable for assessing blood coagulation status in a patient. These may also be adapted to assess fibrinolytic status in a patient.

A wide variety of laboratory clotting tests are based on the phenomenon of measuring as an endpoint, a change of phase when a test solution changes from a liquid to a coagulated form. This change is due to the conversion of a soluble plasma protein fibrinogen to an insoluble one, fibrin by the action of the enzyme thrombin. The reverse change is also made use of in tests where one is measuring the lyric activity of a solution, whereby insoluble fibrin is broken down to soluble degradation products by the enzyme plasmin.

For example, blood clotting tests are important to assess likelihood of bleeding in patients treated with anticoagulants or with haemostatic defects. The endpoint of the most frequently performed clotting test, the skin bleeding time, is the cessation of blood flow from a standardised skin incision. This is usually determined by the periodic blotting of the wound site until blood flow from the wound ceases. This test is particularly prolonged by platelet defects. Other clotting tests are usually carried out by mixing test plasmas with specific reagents and timing to an endpoint when the mixture suddenly clots. The clotting endpoint is usually determined physically, as in a tilt-tube, or optically by increased turbidity, as in a photoelectric clotting machine.

This current innovation has been stimulated by a number of precursore developments. The first of these is the use of convenient dry cards such as the Nyco Card (Nyco Med Pharma) for rapidly testing antibody reactions (e.g. FDP, D-dimer). These devices comprise porous modules which are faced with an immunoreactive membrane. Test samples are applied to such surfaces and are drawn through by capillary action. Antigens or antibodies for test are quantitated by a color reaction after sequential washing and incubation steps. Secondly, small capillary coagulation testing devices have also recently been developed. These are based on blood or plasma drawn into a small capillary with coagulation detected using either a laser (Bio Track, Ciba-Corning) or pressure sensing systems (Nyco Med). One such device features dry coagulation reagents while the other relies on uncoated glass capillaries.

Unfortunately, these prior art devices are quite complex requiring laser or pressure sensing equipment.

It will be clear to persons skilled in the art that there is a need for simpler, more convenient and adaptable methods and apparatus for measuring the susceptibility of liquids to coagulate or lyse over currently existing methods and apparatus. It is desirable to provide small testing modules which may be used at the bedside in a portable form or alternatively can be assembled together to process much larger numbers of samples in a central laboratory.

Currently there is a significant market for rapid portable methods in the coagulation/lysis testing area. Larger laboratories usually purchase expensive sophisticated equipment for massive scale operation. Small inexpensive bedside testing units have an important role in a number of clinical situations especially where prompt interpretation of patient results is required and when screening tests are only rarely positive.

SUMMARY OF THE INVENTION

In order to ameliorate the disadvantages of the prior art it is proposed to provide a method and apparatus for determining the propensity of a test sample to change between a coagulated state and a liquid state which offers a choice over the prior art and which, at least in the preferred embodiments, is cheaper and easier to manufacture and use as compared to prior art devices.

In a first aspect, the present invention provides a method for detecting the propensity of a blood sample to change from a liquid state to coagulated state comprising the steps of;

(i) providing a porous sheet, at least one surface of the porous sheet being in contact with an impervious layer, (ii) applying the blood sample to an exposed surface of the sheet, (iii) allowing the sample to spread through a part of the sheet, and (iv) measuring a parameter indicative of the extent of spread of the sample in the sheet and/or the rate of spread of the sample in the sheet which is indicative of the propensity of the blood sample to coagulate.

In a second aspect, the present invention provides an apparatus for detecting the propensity of a blood sample to change between a liquid state and a coagulated state comprising a porous sheet, an impervious layer in contact with one surface of the sheet and a coagulation/lysis detection means, the detection means being adapted to measure a parameter indicative of the extent of spread of the sample in the sheet and the rate of spread of the sample in the sheet.

The present inventive method and apparatus operate as follows. As the blood sample is applied to the porous sheet, it disperses out from the application point across the area of the sheet. As this liquid disperses, the leading edge of the liquid continually comes into contact with the clotting agent. One or more clotting agents can be present in the porous phase in discrete zones allowing sequential mixing of test sample liquids with them. Eventually, this leading edge begins to coagulate reducing further spreading of the sample through the porous sheet. When the leading edge of the sample has fully coagulated, the rate of further spread of the sample in the porous sheet is virtually zero and the area of the spread sample is constant. It will be clear to persons skilled in the art, therefore, that by measuring a parameter indicative of the extent of spread of the sample in the porous sheet and/or the rate of spread of the sample in the porous sheet, we may obtain an accurate measurement of when coagulation has occurred.

In one embodiment of the present invention, the parameter measured is the area covered by the spread sample or the rate at which this area grows. This parameter may be measured by any appropriate optical means even the human eye especially if whole blood samples are applied. If one uses such an optical measurement means with plasma samples it is preferred to include a dye in the test sample to assist visual detection or to impregnate a part of the porous sheet with a dye.

Using such an optical measurement means, one may apply the test sample to the porous sheet and measure the extent of the area covered by the spread sample prior to coagulation giving a measurement of when coagulation occurred. Alternatively, an operator may monitor the rate of growth of the area of the spread sample. Graduations may be incorporated on at least one of the impervious layers of the inventive apparatus to assist in measuring the extent of sample spread. When the rate of growth of the area approaches zero, coagulation has occurred.

In another embodiment of the present invention, the appropriate parameter for detecting coagulation may be measured by an electrical sensing means. For example, thin electrodes may be provided on either surface of the porous sheet. The conductivity or electrical impedance between these electrodes depends upon the wetted area between them. Prior to application of the test sample to the porous sheet, the impedance between the electrodes will approach infinity with conductivity at zero. As the test sample spreads through the sheet, it increases the wetted area between the electrodes leading to a decrease in impedance and increase in conductivity. As the test sample further spreads out through the sheet impedance will further reduce and conductivity will be further increased. It can therefore be seen that the impedance/conductivity between the electrodes is a measure of the extent of spread of the sample in the sheet.

By examining the rate of change of the conductivity/impedance between the electrodes one may measure the rate of spread of the sample in the medium. As discussed above, when the leading edge of the sample coagulates further spread of the sample through the porous sheet is greatly reduced depending on the amount and permeability of the fibrin formed therein. Accordingly, when the leading edge of a normal sample coagulates there is virtually no increase in conductivity or corresponding decrease in impedance with time. By monitoring the change in conductivity/impedance between the electrodes one may detect when coagulation occurs since at this point the rate of change of conductivity/impedance will approach zero.

If the fibrin formed in the sheet by clotting reactions is subsequently lysed by the fibrinolytic plasmin then further penetration of the liquid sample into the porous sheet will take place. Thus the time at which conductivity resumes its increase can be used to indicate fibrinolytic susceptability within a sample.

BRIEF DESCRIPTION OF THE DRAWINGS

The present invention will now be described by way of example only with reference to the accompanying drawings in which.

DESCRIPTION OF THE PREFERRED EMBODIMENTS

Figure 1:
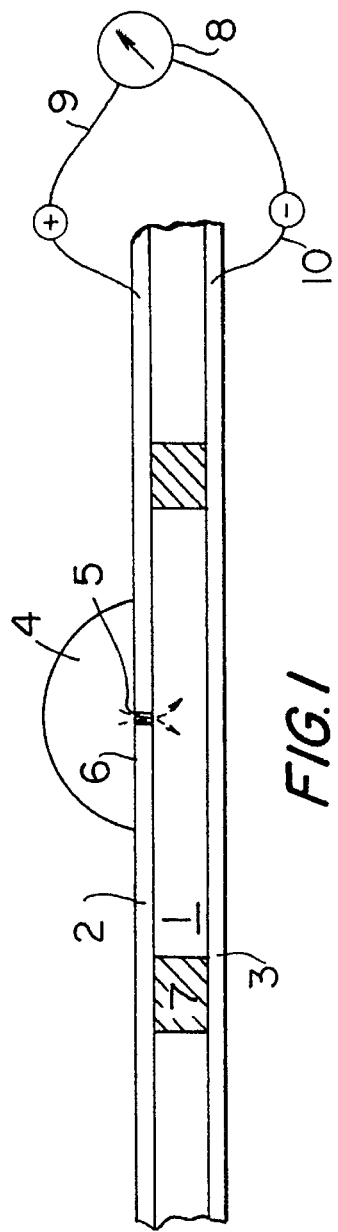
FIG. 1 is a longitudinal cross-sectional view of an apparatus for measuring the susceptability of a liquid to coagulate according to a first embodiment of the present invention.

Turning firstly to FIG. 1, the inventive apparatus comprises a porous sheet 1 sandwiched between surface electrodes 2 and 3 across which a small voltage is applied. A test sample 4 of a liquid may be applied to the top surface 6 of electrode 2 to be drawn down through aperture 5 and spread through sheet 1.

Prior to application of the test sample, the resistance between surface electrodes 2 and 3 will approach infinity with conductivity at zero. If it is necessary to measure the time for coagulation of the test sample, application of the test sample 4 will automatically reduce the resistance between electrodes 2, 3 thereby indicating a "start" time on recorder device 8. As the test sample is drawn down and through sheet 1, it wets the area between electrodes 2 and 3 reducing resistivity and increasing conductivity.

The test sample 4 will spread through sheet 1 as discussed above covering an ever increasing area. As the sample spreads its leading edge progressively mixes with the clotting agent impregnated through the porous sheet 1. Eventually the leading edge of the sample will coagulate and clots 7 will be formed.

As will be clear to persons skilled in the art, the speed at which the sample coagulates is dependent on the properties of the sample itself as well as on the type and quantity of clotting agent or lytic agent in the sheet of absorbent medium. Subsequent lysis of the clot resulting in further dispersion of liquid into the sheet depends on the presence of fibrinolytic activator and its specific effect.

Figure 5:
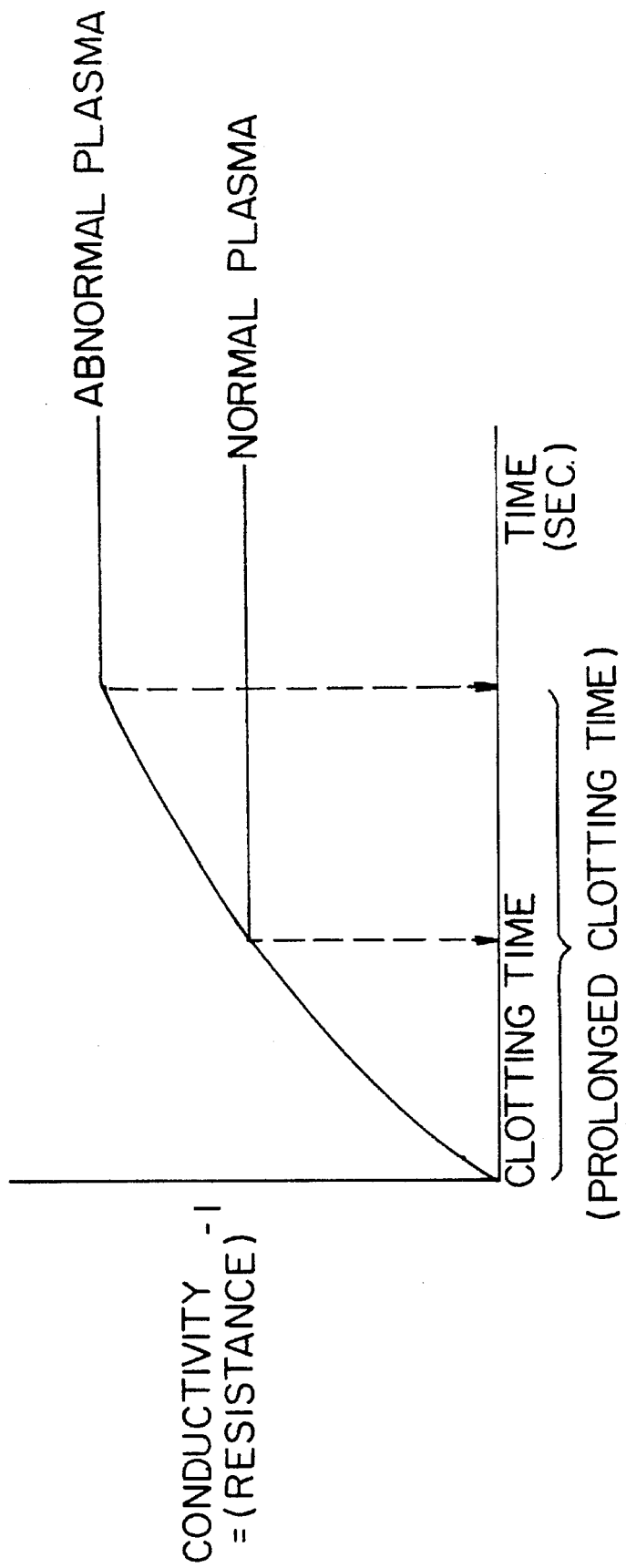
FIG. 5 is a graph describing the relationship between conductivity and time measurements for a typical clotting time and fibrinolytic resistance test.

Chart recorder 8 connected to electrodes 2 and 3 via leads 9 and 10 records the conductivity/resistivity between the electrodes for example as shown in FIG. 5. As discussed above, once clots 7 are formed the rate at which the sample 4 spreads is reduced leading to a corresponding reduction in the rate of increase of the conductivity between the electrodes. By monitoring the conductivity/resistivity or the change in conductivity/resistivity between the electrodes as a function of time an accurate indication may be obtained of when the sample coagulates.

In preliminary studies, the porous sheet used comprised a thin filter paper which served to absorb and diffuse the plasma used in the test. It is preferred that the sheet 1 comprise a thin sheet so that even a small 0.05 ml sample spreads into a large area. The material of the membrane should not absorb water from the blood or plasma samples as this leads to an unpredictable spreading pattern. Preferably, the sheet 1 includes small even pores so that spreading of the absorbed test sample is regular and susceptible to occlusion by fibrin and/or platelet aggregates. The sheet preferably contains dry stabilized reagent to clot the sample so that the fibrin formed and/or platelet aggregate significantly retard the subsequent spreading of the sample.

Preferably clotting reagents which may be included within this medium sheet 1 include tissue factor (thromboplastin), contact activator and phospholipid for use in a APTT-like test and various other coagulation activators including Russell's viper venom, contact product (activated factor XI) and platelet activating agents. Thrombin and activated factor X may be also applied with stabilizers to such papers for tests to be used for monitoring antithrombotic drugs such as low molecular weight heparin. Such tests yield prolonged clotting times relative to normal plasma and may be used to assess anticoagulant status. Fibrinogen levels may be interpreted from the rate of change of conductance after clotting by a reference thrombin like enzyme concentration has occurred. High fibrin content results in less rapid capillary flow and less change over time. Low fibrinogen levels yield more porous clot allowing more permeability through the clot.

Specific assays for factor VIII are based on haemophilic (factor VIII deficient) plasma dried in a zone separate from an APTT reagent dried on the membrane so that it is dissolved by diluted test plasma first. Assays for other clotting factors including platelets may be developed similarly using specific deficient plasmas. The other component which may be included in medium 1 is calcium which will be applied as non-deliquescent salts in a zone furthest from the application point. The concentration of this will be adjusted to be about 0.025M and of the other reagents will be optimal for test sensitivity with zone spreading achieved in 30–60 sec from the time of sample application.

Buffer additives and salts are required to yield physical conditions of high pH (in the range of 7.5–8.5) and ionic strength (in the range of 0.1–0.2M [NaCl] under which fibrin gels are least permeable.

Other main components which may be included in the medium are surfactants and hydrophilic polymers. Surfactants control the surface tension at the liquid interface and this is important in regulating the rate of spreading. Hydrophilic polymers in appropriate concentrations are required to control the rate of dissolution of dry components and the speed of transport of liquid through the porous medium. Gelatin coating of the porous phase enhances the adhesion of the fibrin clot. Specific polymers such as gum arabic also enhance the restrictive effects of fibrin (when it forms) on the rate of liquid transport. Typical hydrophilic colloids of use here include polyvinyl alcohol and sodium alginate at 1% concentration. Fibrinogen, bovine and/or modified covalently with polymers may be added to enhance fibrin gel strength in some tests. The concentrations of such polymers need to be controlled to avoid irregular spreading of liquid through the membrane due to high viscosity at the leading edge. Other dried components include well known protein stabilizers, lactose, antioxidants and sodium azide.

In some circumstances two incompatible components (for example specific factor deficient plasmas and calcium) for a clotting test system may be introduced into a test module in two separate zones or on two separate over-lapping sheets. Thus different optimal conditions for each component can be maintained during storage and they will mix together only when wetted by test sample. For fibrinolytic studies, streptokinase, urokinase or tissue plasminogen activator will be included in the clotting reagent mixture. After clotting has occurred a subsequent increase in conductivity or decrease in impedance indicates the time required for fibrinolysis in individuals. This is often prolonged in patients resistant to fibrinolysis, for example those having antibodies against streptokinase.

The present inventive method and device may also be applied to a skin bleeding time procedure in which blood issuing from a standardized wound is progressively quantitated by the increasing conductivity between a surface electrode and underlying skin.

Figure 4:
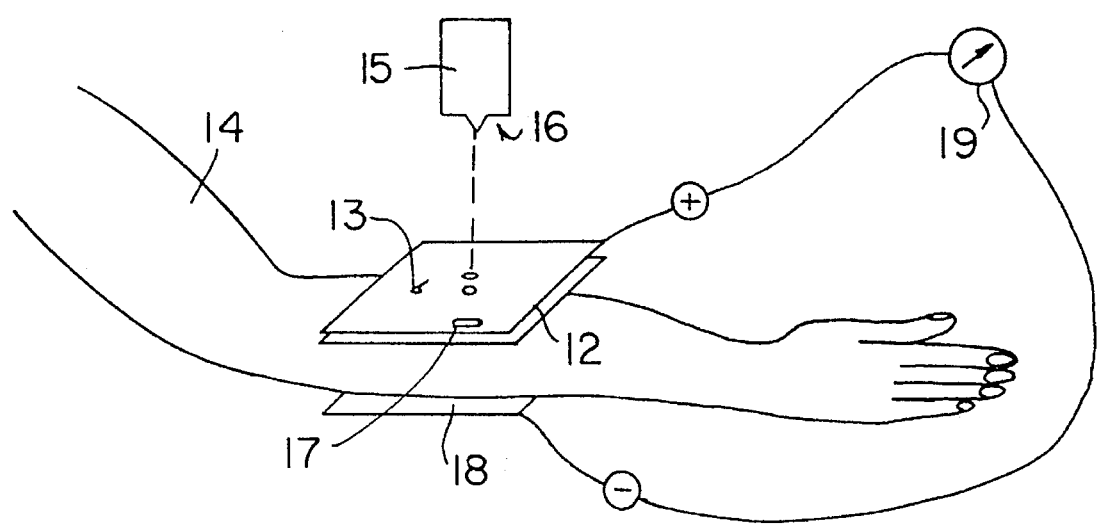
FIG. 4 is a perspective view of an apparatus to measure the susceptability of a liquid to coagulate according to a fourth embodiment of the present invention.

As shown in FIG. 4 the porous sheet 12 may be placed directly on the wound of a patient. This embodiment is particularly suitable for obtaining a skin bleeding test from a patient. In this embodiment, only one surface of the sheet 12 is covered by an impervious layer so that the blood emanating from the wound of the patient may be directly applied to the exposed side of sheet 12.

In FIG. 4, the impervious layer on the exterior side of sheet 12 is provided by surface electrode 13. The combined sheet/electrode assembly is placed directly against the arm 14 of a patient. To obtain a sample of blood from the patient, a lancet 15 is forced through top layer 13 and porous sheet 12 into the arm 14 of the patient.

The lancet has a standardised cutting surface to produce a standard size wound 17. As blood issues from the wound, it is drawn into and dispersed in sheet 12 as discussed above. Bottom electrode 18 is brought into contact with the skin of the patient well removed from wound site 17. It is preferred that no coagulation influencing agent is included in sheet 12 so as not to interfere with the patient's normal blood clotting. FIG. 4 shows a typical arm incision. However, it may be preferable to apply such an improved device to a site on the lower leg to simplify the need for increased venous blood pressure.

Skin bleeding time tests of this type are usually intended to measure procoagulant mechanism involving blood platelets, collagen and tissue factor released at the wound site. To achieve better specificity for platelet function, weak anticoagulants may be used in the absorbent medium sheet 12 so that platelet agglutination becomes relatively more important. Additionally platelet agonists such as ADP or collagen may be induced in the membrane.

If it is desired to measure the coagulation properties of blood from a patient, it is preferred that the assembly is heated so the sample remains at a constant temperature, preferably 37° C. i.e. the temperature of the human body. This may be accomplished by simply holding the inventive apparatus against the skin of the patient or alternatively a separate heating/cooling means may be provided.

As discussed above, as the sample of blood from the patient spreads through porous medium 12 it may be monitored with chart recorder 8 set to measure electrical resistivity or conductivity between electrodes 18 and 13.

It is preferred that very low voltage levels are used in the inventive device e.g. less than one volt, in order to avoid polarization at the electrode-liquid interface. The applied voltages may be constant or preferably pulsed or alternating. If pulsed voltages are used the responses may be analysed by an oscilloscope for additional impedance changes to confirm clotting.

Figure 3:
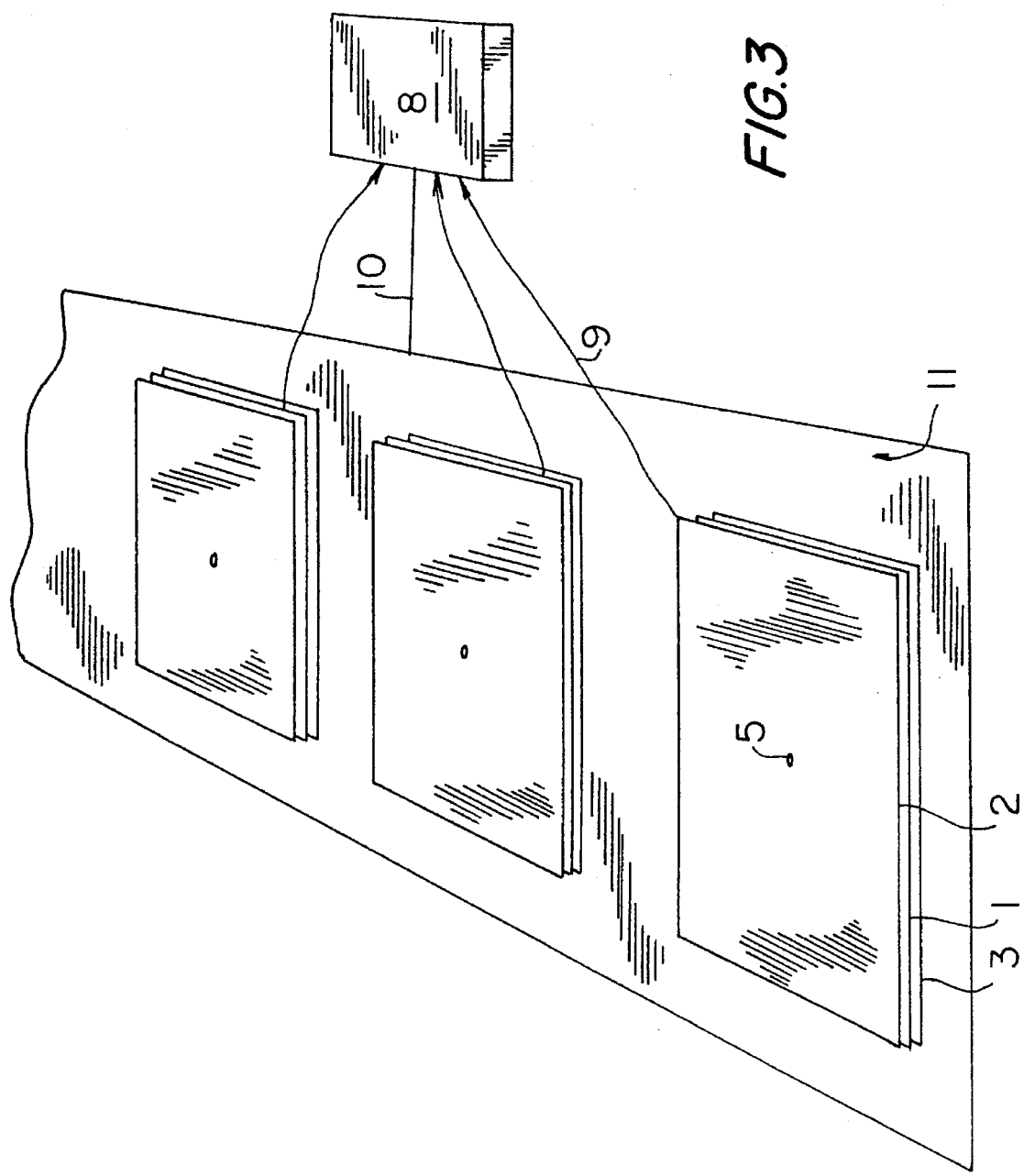
FIG. 3 is a perspective view of an apparatus to measure the susceptability of several liquids to coagulate according to a third embodiment of the present invention.

As shown in FIG. 3, individual modules comprising the absorbent medium 1 with electrodes 2, 3 on either surface may be clamped to a flat thermostatted surface 11 to maintain the assembly and sample at. 37° C. This allows several modules to be used at the same time, each module being connected to chart recorder 8. Different modules may include a porous sheet 1 which has been treated with a different coagulation influencing agent. Application of identical samples to each of these modules allows an operator to ascertain the effectiveness of each coagulation influencing agent on identical liquid samples.

In another embodiment electrodes 3 may be deleted with plate 11 acting as a common negative backing plate for several testing modules assembled thereon.

It is also within the scope of the present invention to incorporate insulating films on the surface electrodes. These insulating portions may be oriented at particular positions on the surface electrodes in order to measure the extent of spread of the sample. To explain, as the sample spreads in the porous sheet it increases the conductivity and decreases the resistivity between the electrodes. When the spreading liquid reaches an insulating film there will be a temporary cessation of charge in conductivity indicating the position of the sample spread in the sheet.

In another embodiment of the present invention if simple voltage analysis is preferred over conductivity/resistivity measurement, the surface electrodes may be made from non-inert dissimilar materials, for example aluminium and copper. Contact with the test sample, therefore will generate a small temporary voltage difference. This electric potential can directly be used to monitor the spread of sample liquid in the porous sheet.

The electrical conductivity/resistivity measurements may be accumulated by a computer interface with subsequent analysis and/or conversion to conventional units e.g. seconds or ratios relative to normal through simple programming methods. It will be clear to persons skilled in the art that monitoring the resistivity or conductivity between electrodes over time will yield a more precise indication of clotting times than possible via subjective visual or optical analysis.

As an example, the relationship between electrical resistance and amount of test sample within a 0.2 mm absorption medium sheet is shown in Table 1.

TABLE 1

| Volume Plasma Absorbed | Resistance $\Omega$ |
| --- | --- |
| 0μl | ∞ |
| 5 | 40 |
| 10 | 25 |
| 20 | 16 |
| 50 | 12 |

Figure 2:
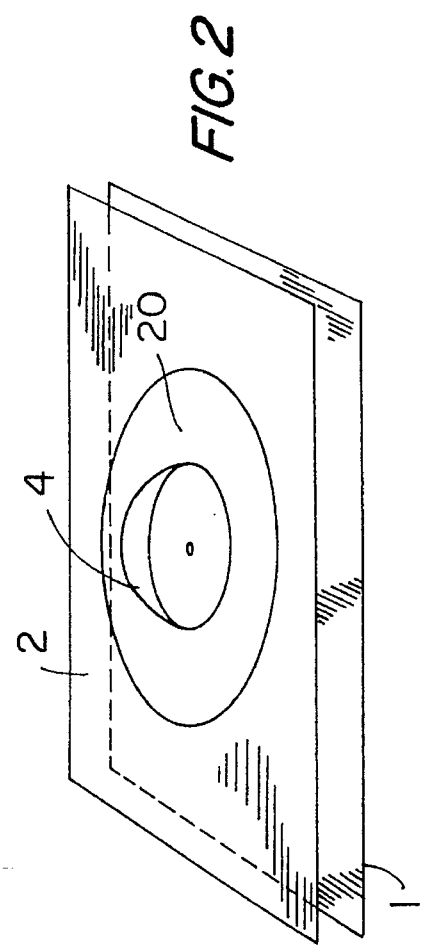
FIG. 2 is a schematic perspective view of an apparatus to measure the susceptability of a liquid to coagulate according to a second embodiment of the present invention.

An alternative embodiment of the present invention is shown in FIG. 2 which includes an impervious transparent top sheet 2 allowing optical measuring of the extent of spread of the sample in the sheet and/or the rate of spread of the sample in the sheet. This embodiment may include one impervious layer, with the exposed side of the porous sheet being directly applied to a patient similar to the embodiment of FIG. 4.

Alternatively, the porous medium 1 may be sandwiched between impervious layers one of which is transparent.

This embodiment allows a person to simply view the extent of spread of the sample in the sheet and or the rate of spread of sample in the sheet.

Graduations or reference points may be included on transparent top sheet 2 to assist in optical measuring of the sample spread. It is also possible to view optical changes with thin electrode wires overlying each clot-sensing zone in strips of porous medium.

Figure 6:
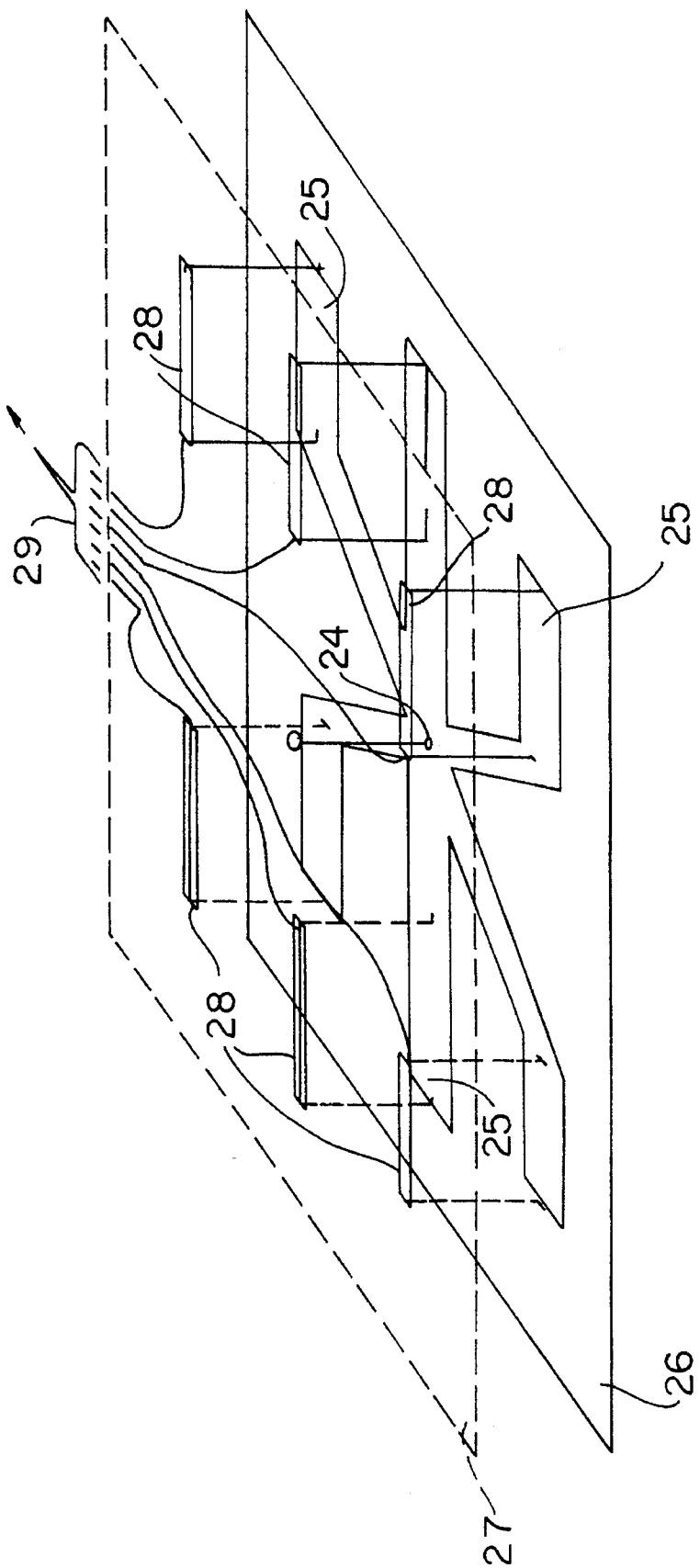
FIG. 6 is a schematic perspective view of a device for measuring the susceptability of a liquid to coagulate and lyse according to a fifth embodiment of the present invention.

In another embodiment of the present invention, as shown in FIG. 6, the porous sheet 1 is provided with a plurality of identical arms 25 radiating from a central sample application point 24. Once again, at least one surface of the sheet 1 is underlayed by an impervious conducting layer 26. Optional impervious layer 27 may also be included to contain discrete thin wire electrodes 28 overlying each clot-sensing zone leading to recorder connection 29.

As previously discussed, when the sample is applied to the porous sheet it disperses throughout the sheet, in this case along each of the arms 25. Each arm preferably includes a different clotting/lysis agent with one arm acting as a control and having no clotting/lysis agents.

With each arm 25 being impregnated with a different clotting/lysis agent, coagulation or lysis takes place at a different point along each arm 25. By monitoring the extent of spread of a sample in each arm and/or the rate of spread of the sample in each arm, the effectiveness of the various clotting or lysis agents may be determined.

Once again the measurement of the extent of spread of the sample or rate of spread may be determined visually or electrically as discussed above.

It will be clear to persons skilled in the art that the present inventive method and apparatus may equally be used to measure the propensity of a liquid to change from a coagulated state to a liquid state. As discussed briefly above, after clotting of the test sample has occurred the clot may become subject to lysis by a lytic agent present already in the clotting agent which returns the sample to a liquid state. Indeed, where the porous sheet is bounded on both surfaces by impervious layers, the clot formed may return to a liquid state over time without the addition of a lytic agent.

It can therefore be seen that after clotting has occurred, one may determine the susceptability of a liquid to change from a coagulated state to a liquid state by measuring a parameter indicative of the speed of lysis.

To explain, once the test sample changes from its coagulated state to its liquid state, the sample will begin to spread once more leading to an increase in the extent of spread of the sample and/or the rate of spread of the sample in the sheet. This further spreading of the sample may be noticed visually as discussed above or measured electrically since the further spreading of the sample will increase conductivity or decrease resistivity between the surface electrodes.

The use of the porous sheet allows the inventive apparatus and method to be adapted to test for a large variety of individual clotting/lysis factors. A complete coagulation/lysis profile of an individual may be achieved quickly and cheaply by combining a panel of inventive test modules.

The present invention allows an individual to purchase a number of modules bounded by one or two impervious sheets or surface electrodes. This person may then apply the test sample, e.g. blood to the porous sheet by direct contact with the skin or via an appropriate sampling means. Coagulation/lysis of the sample may be detected by measurement of an appropriate parameter indicative of the extent of spread of the sample in the sheet and/or the rate of spread of sample in the sheet. In the embodiments shown, visual detection or electrical measurement of the area of the spread sample is used however any other parameter is equally applicable.

It is believed that the present invention will excel not only in the medical but also veterinary fields where simple inexpensive bedside testing units have an important role particularly where prompt interpretation and diagnosis of the patient is required.

I claim:

1. A method of determining a propensity of a blood sample to change from a liquid state to a coagulated state, said method comprising the steps of:

a) providing a porous sheet, at least one surface of said porous sheet being in contact with an impervious layer;

b) applying the blood sample to an exposed surface of the porous sheet so that said blood sample spreads through the porous sheet; and c) after the applying of step b), measuring at least one of a spreading extent and a spreading rate of said blood sample in said porous sheet by one of optical means, measuring an electrical conductivity across the porous sheet, measuring an electrical potential across the porous sheet and measuring an electrical resistance of the porous sheet, to determine the propensity of said blood sample to change from a liquid state to a coagulated state.

2. The method as defined in claim 1, further comprising applying a lytic agent to the porous sheet with the blood sample after the blood sample has coagulated in the porous sheet to lyse the coagulated blood sample in the porous sheet and form a lysed sample and measuring at least one of a spreading extent and a spreading rate of said lysed sample in said porous sheet by one of optical means, measuring an electrical conductivity across the porous sheet, measuring an electrical potential across the porous sheet and measuring an electrical resistance of the porous sheet, to determine the propensity of said blood sample to change from a coagulated state to a liquid state.

3. The method as defined in claim 1, further comprising impregnating the porous sheet with a clotting agent and exposing said clotting agent to at least one component of said blood sample to cause coagulation of the blood sample.

4. The method as defined in claim 2, wherein said lytic agent is a fibrinolytic activator.

5. The method as defined in claim 1, wherein said porous sheet is between said impervious layer and another impervious layer.

6. The method as defined in claim 1, wherein said spreading extent is measured by an area over which said blood sample has spread in said porous sheet.

7. The method as defined in claim 1, wherein said spreading extent is measured by a distance over which said blood sample has spread in said porous sheet.

8. The method as defined in claim 1, further comprising providing a surface electrode on each of two opposite surfaces of the porous sheet.

9. The method as defined in claim 1, wherein the porous sheet has a central portion and a plurality of arms connected to the central portion, and further comprising applying a member selected from the group consisting of coagulation agents and lytic agents to each of said arms and wherein, during the applying of the blood sample to the porous sheet, the blood sample is applied to the central portion of the porous sheet.

10. The method as defined in claim 1, further comprising maintaining the blood sample at a constant temperature after the applying of the blood sample to the porous sheet.

11. The method as defined in claim 10, wherein the constant temperature is substantially 37° C.

12. The method as defined in claim 1, further comprising impregnating the porous sheet with a dye before the applying of the blood sample to the porous sheet.

13. The method as defined in claim 1, further comprising dyeing the blood sample before the applying of the blood sample to the porous sheet.

14. The method as defined in claim 1, further comprising making an incision through a portion of skin of a patient to obtain the blood sample.

15. The method as defined in claim 14, further comprising providing a first surface electrode on an exterior surface of the porous sheet and applying a second surface electrode to another skin portion of the patient remote from the incision.

16. An apparatus for determining a propensity of a blood sample to change from a liquid state to a coagulated state, said apparatus comprising a porous sheet, an impervious layer contacting one surface of the porous sheet and measuring means for measuring at least one property of the porous sheet after a blood sample has been applied to the porous sheet, wherein said at least one property is selected from the group consisting of a spreading extent of the blood sample in the porous sheet and a spreading rate of the blood sample in the porous sheet, and wherein said measuring means is selected from the group consisting of means for optical measurement, means for measuring an electrical conductivity across the porous sheet, means for measuring an electrical resistance of the porous sheet and means for measuring an electrical potential across the porous sheet.

17. The apparatus as defined in claim 16, wherein the porous sheet has an impregnated clotting agent, said clotting agent causing the blood sample to coagulate when at least one component of the blood sample is exposed to the clotting agent.

18. The apparatus as defined in claim 16, wherein the porous sheet has an impregnated lytic agent, said lytic agent causing a coagulated blood sample in the porous sheet to lyse when at least one component of the coagulated blood sample is exposed to the lytic agent.

19. The apparatus as defined in claim 16, further comprising another impervious layer applied to the porous sheet on a surface of the porous sheet opposite to the surface contacted by the impervious layer.

20. The apparatus as defined in claim 16, wherein the measuring means for measuring said at least one property comprises said means for optical measurement.

21. The apparatus as defined in claim 16, wherein the measuring means for measuring said at least one property comprises electrical sensing means.

22. The apparatus as defined in claim 21, wherein the electrical sensing means comprises a surface electrode provided on each side of the porous sheet.

23. The apparatus as defined in claim 16, wherein the porous sheet includes a plurality of arms radiating from a central portion, each of the arms being impregnated with a member selected from the group consisting of clotting agents and lytic agents.

24. The apparatus as defined in claim 16, further comprising means for maintaining the blood sample at a constant temperature.

25. The apparatus as defined in claim 24, wherein the constant temperature is substantially 37° C.

* * * * *